(12) United States Patent
Terrero

(10) Patent No.: US 8,536,348 B2
(45) Date of Patent: Sep. 17, 2013

(54) LACTONE FORMULATIONS AND METHOD OF USE

(75) Inventor: David Terrero, Ensanche Quisquella (DO)

(73) Assignee: Magnachem International Laboratories, Inc., Boca Raton, FL (US)

( * ) Notice: Subject to any disclaimer, the term of this patent is extended or adjusted under 35 U.S.C. 154(b) by 0 days.

(21) Appl. No.: 12/968,508

(22) Filed: Dec. 15, 2010

(65) Prior Publication Data

US 2011/0092588 A1  Apr. 21, 2011

Related U.S. Application Data

(63) Continuation of application No. 11/139,338, filed on May 26, 2005, which is a continuation of application No. 10/172,462, filed on Jun. 12, 2002, now Pat. No. 6,900,242.

(60) Provisional application No. 60/297,875, filed on Jun. 13, 2001.

(51) Int. Cl.
  *C07D 307/02* (2006.01)
  *A01N 43/08* (2006.01)

(52) U.S. Cl.
  USPC .......................................... 549/295; 514/473

(58) Field of Classification Search
  USPC ........................................ 549/295; 514/473
  See application file for complete search history.

(56) References Cited

U.S. PATENT DOCUMENTS

| | | | |
|---|---|---|---|
| 2,624,723 A | 1/1953 | McGraw | |
| 2,624,732 A | 1/1953 | Hitchings | |
| 3,203,953 A | 8/1965 | Lucas | |
| 3,210,377 A | 10/1965 | Machleidt | |
| 3,993,771 A * | 11/1976 | Uematsu et al. | 514/473 |
| 4,001,425 A | 1/1977 | Price | |
| 4,613,613 A | 9/1986 | Oguri | |
| 5,242,945 A | 9/1993 | Caufield | |
| 5,250,735 A | 10/1993 | Wong | |
| 5,281,622 A | 1/1994 | Wong | |
| 5,595,756 A | 1/1997 | Bally | |
| 5,646,164 A | 7/1997 | Tzeng | |
| 5,905,089 A * | 5/1999 | Hwang et al. | 514/468 |
| 5,962,460 A | 10/1999 | Tzeng | |
| 5,977,169 A | 11/1999 | Chrusciel | |
| 5,981,575 A * | 11/1999 | Kuhajda et al. | 514/473 |
| 6,180,651 B1 | 1/2001 | Nicolai | |
| 6,222,048 B1 | 4/2001 | Black | |
| 6,232,474 B1 | 5/2001 | Brandenburg | |
| 6,395,724 B1 | 5/2002 | Judice | |
| 6,686,390 B2 | 2/2004 | Pal | |
| 6,900,242 B2 | 5/2005 | Terrero | |
| 7,323,495 B2 | 1/2008 | Terrero | |
| 2005/0101663 A1 | 5/2005 | Terrero | |
| 2005/0239877 A1 | 10/2005 | Gomez | |
| 2008/0125484 A1 | 5/2008 | Terrero | |

FOREIGN PATENT DOCUMENTS

| | | |
|---|---|---|
| EP | 0712843 | 11/1999 |
| JP | 51125722 | 11/1976 |
| JP | 54084564 | 7/1979 |
| JP | 56128776 | 10/1981 |
| JP | 580199413 | 6/1983 |
| JP | 62026221 | 2/1987 |
| JP | 64016776 | 1/1989 |
| JP | 01163175 | 6/1989 |
| JP | 200237797 | 2/2002 |
| WO | 9629392 | 9/1996 |
| WO | 9718806 | 5/1997 |
| WO | 9728147 | 8/1997 |
| WO | WO 9843966 * | 3/1998 |
| WO | 9840078 | 9/1998 |
| WO | 9843966 | 10/1998 |
| WO | 9953915 | 10/1999 |
| WO | 0139720 | 9/2001 |
| WO | 0164913 | 9/2001 |
| WO | 02064160 | 8/2002 |
| WO | 02100854 | 12/2002 |

OTHER PUBLICATIONS

Shlewer et al. J. Med.Chem., 1990, 23, 1031-1038.*
Sanyal et al. J. Med.Chem., 1996, 29, 595-599.*
J. C. M. Beijersbergen, Recl. Tray. Chim. Pays-Bas, 91, 1193 (1972).*
Schroeder Pflanzenschutz (1972), 79(1), 1-9. English Translation.*
Briskin, Plant Physiology, 2000, vol. 124, pp. 507-514.*
Neerman M. F. International Journal of Aromatherapy, 13, 114, 2003.*
Heindel et al. Journal of Pharmaceutical Sciences (1981), 70(1), 84-6.*
Facely et al. J. Pharm. Pharmacol. 1999, 51: 1555-1560.*
Haitao, et al., "Anti-tumor and anti-inflammatory activity of nature products and structural analogues thereof with alpha-methylene-gamma-butyrolactone", Chin. J. of Medicinal Chem., 4(2):137-149 (1994).

(Continued)

*Primary Examiner* — Nizal Chandrakumar
(74) *Attorney, Agent, or Firm* — Pabst Patent Group LLP

(57) ABSTRACT

Compounds of Formulae Ia

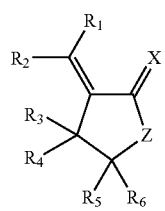

Formula Ia wherein $R_1$-$R_9$ taken independently are preferably a hydrogen atom, a halogen atom, a hydroxyl group, or any other organic groups or grouping, Z and X are independently and preferably a heteroatom such as oxygen, sulfur, or nitrogen groupings are useful for treatment of bacterial and fungal infections.

22 Claims, No Drawings

(56) References Cited

OTHER PUBLICATIONS

Adam, et al., "Stereoelectronic control 1,3 of the diastereoselectivity in the photooxygenation (Schenck Ene Reaction) of an electron-poor allylic alchohol and its ethers", J. Organic Chem., 63(2):226-227 (1998).

Baldwin, et al., 5-endo-Trigonal reactions: a disfavoured ring closure, J. Chem Soc. Chem Comm., 18:736-38 (1976).

Benezra, "Molecular recognition in allergic contact dermatitis to natural products", Pure & Appl. Chem, 62(7):1251-58 (1990).

Burke and Pacofsky, "The ester enolate claisen rearrangement", Tetra. Lett., 27(4):445-448 (1986).

Burke, et al., "Synthesis or ethisolide, isoavenaciolide and avenciolide", J. Organic Chem., 57(8):2228-2235 (1992).

Cassady, et al., "Potential antitumor agents. Synthesis, reactivity, and cytoxicity of alpha-methylene carbonyl compounds", J Med Chem. ,21(8):815-9 (1978).

Cavallito and Haskell, "±-methylene butyrolactone from *Erythronium anerucanum*", J. Am. Chem. Soc., 68 (11), pp. 2332-2334 (1946).

Chan, "Mechanisms of Renal Allograft Rejection," Transplant rejection and its Treatment (Tracy 12), Dec. 12, 2008.

Chen, et al., "Cytotoxic butanolides from Litsea Akoensis", Phytochemistry, 49 (3);745-50 (1998).

Chen, et al., "-Methylene—butyrolactones: synthesis and vasorelaxing activity assay of coumarin, naphthalene, and quinolone derivatives", Chem. Pharm. Bull., 46(6): 962-965 (1998).

Chester, et al., "±-methylene butyrolactone from *Erythronium americanum*," J. Am. Chem. Soc., 68:2332-4 (1946).

Corbet and Benezra, "Allergenic alpha-methylene-gamma-lactones", J. Organic Chem., 46(6)1141-1147 (1981).

Fuchino, et al., "New sesquiterpene lactones from *Elephantopus mollis* and their leishmanicidal activities", Planta Me 67:647-653 (2001).

Gelin and Chantegrel, "Synthesis of 3-Formyltetronic acid and enamine derivatives", J. Heterocyclic Chem., 18:663-665 (1981).

Grigg, at al., "X=Y-ZH Systems as potential 1,3-dipoles part 35. Generation of nitrones from oximes. Class 3 processes. Tandem Intramolecular Michael addition (1,3-azaprotio cyclotransfer)-intermolecular 1,3-dipolar cycloaddition reactions.1,2" Tetrahedron, 48(33): 6929-6952 (1992).

Hall, et al., "Anti-inflammatory activity of sesquiterpene lactones and related compounds", J. Pharm, Sci., 68(5):537-42 (1979).

Hein, et al., "Bombardolides: new antifungal and antibacterial gamma-lactones from the coprophilous fungus *Bombardioidea anartia*", J. Nat. Prod., 64(6):809-12 (2001).

Hidaka, at al., "Inhibition of polymorphonuclear leukocyte 5-lipoxygenase and platelet cyclooxygenase by alpha-(3,5-di-tert-butyl-4-hydroxybenzylidene)-gamma-butyrolacto ne (KME-4), a new anti-inflammatory drug", Jpn. J. Pharmacol., 38(3):267-72 (1985).

Hoffmann and Rabe, "Synthese and biologische activitat von ±-methylen-$^3$-butyrolactonen," Angewandte Chemie, 97(2):96-112 (1985).

Hopkins, et al., "Deletion of mouse rad9 causes abnormal cellular responses to DNA damage, genomic instability, and embryonic lethality." Molecular and Cellular Biology, 24 (16) : 7235-7248 (2004).

Howie, at al., "Synthesis of alkyl-substituted ±,$^2$-unsaturated $^3$-lactones as potential antitumor agents," J Med Chem., 17(8):840-3 (1974).

Huang, at al., "Synthetic and cytotoxic studies of -methylene—butyrolactone bearing pyrimidines", Kaohsiung J. Med. Sci., 9:707-711 (1993).

Hutchinson, "A synthesis of tulipalin A and B and the acylglucoside, tuliposide A, fungitoxic agents from *Tulipa gesneriana*. Carbon-13 nuclear magnetic resonance analysis of anomeric configuration in acylglucosides", J. Org. Chem., 39(13):1854-3 (1974).

Ingolfsdottir, et al., in vitro susceptibility of Helicobacter pylori to protolichesterinic acid from the lichen *Cetraria islandica* Antimicrob Agents Chemother. 1997 41(1 ):215-7 (1997).

Kuhajda, et al., "Synthesis and antitumor activity of an inhibitor of fatty acid synthase", Proc. Natl. Acad. Sci. USA, 97(7):3450-3454 (2000).

Kunes, et al., "Synthesis and antifungal activity evaluation of 3-hetary1-2,5-dihydrofuran-2-ones", Collect. Czech. Chem. Commun., 66:1809-1830.

Kwon, et al., "New cytotoxic butanolides from *Lindera obtusiloba* BLUME", Chem. Pharm. Bull. (Tokyo)., 48(5):614-6 (2000).

Lee, et al., "Sesquiterpene antitumor agents: inhibitors of cellular metabolism", Science, 196:533-535 (1977).

Lee, et al., "Synthesis and anticancer evaluation of certain -methylene—(4-substituted phenyl)-g-butyrolactone bearing thymine, uracil, and 5-bromouracil", Bioorg. & Med. Chem., 9:241-244 (1999).

Lenz, et al., "A test battery of bacterial toxicity assays and comparison of LD50 values," Toxicity Assessment, 4(1):43-52 (1989).

Maria, et al., "Gastric anti-ulcer activity of several -unsaturated carbonyl compounds in rats", Biol. Pharm. Bull., 23(5):555-557 (2000).

Meyerkord, et al., "Loss of Hus 1 sensitizes cells to etoposide-induced apoptosis by regulating BH3-only proteins." Oncogene, 27(58): 7248-7259 (2008).

Murray and Norton, "The design and mechanism of palladium catalysts for synthesis of methylene lactones by cyclocarbonylation of acetylenic alcohols", J. Amer. Chem. Soc., 101:4107-19 (1979).

Nishide, et al., "Total asymmetric syntheses of (+)-blastomycinone and related gamma-lactones", Tetrahedron, 50(28):8337-8338 (1994).

Panda, et al., "Mechanism of action of alpha-methylene-gamma-lactone derivatives of substituted nucleic acid bases in tumour cells", Chemotherapy, 35:174-180 (1989).

Park, et al., "Anti-helicobacter pylori effect of costunolide isolated from the stem bark of *Magnolia sieboldii*," Arch. Parm. Res., 20(3):275-279 (1997).

Paulitz, et al., "A novel antifungal furanone from Pseudomonas aureofaciens", J. Chem. Eco., 26(6):1515-1524 (2000).

Pour, et al., "3-Phenyl-5-methyl-2H,5H-furan-2-ones: tuning antifungal activity by varying substituents on the phenyl ring", Bioorg. Med. Chem. Lett., 10(16):1893-5 (2000).

Prestera, et al., "Chemical and molecular regulation of enzymes that detoxify carcinogens", Proc Natl Aced Sci U S A., 90(7):2965-9 (1993).

Rezanka and Dembitsky, "gamma-Lactones from the soft corals Sarcophyton trocheliophorum and Lithophyton arboreum", Tetrahedron, 57(41):8743-8749 (2001).

Rodriguez, et al., "Biological activities of sesquiterpene lactones", Phytochemistry, 15:1573-1580 (1976).

Rollinson, et al., "The total synthesis of Lauraceae lactones", J. Amer. Chem. Soc., 103(14):4114-4125 (1981).

Sanyal, et al., "New -methylene—lactone derivatives of substituted nucleic acid bases as potential anticancer agents", J. Med. Chem., 29(5):595-599 (1986).

Schlewer, et al., "Synthesis of -methylene—butyrolactones: a structure-activity relationship study of their allergenic power", J. Med. Chem 23:1031-1038 (1980).

Schuster, et al., "Sesquiterpene lactones from Koanophyllon albicaule", Pytochemistry, 31(9):3143-6 (1992).

Simon, et al., "Novel approaches to screen for anticancer drugs using *Saccharomyces cerevisiae*.", Methods in Molecular Biology, 223: 555-576 (2003).

Spring, et al., "Annuithrin, a new biologically active germacranolide from *Helianthus annuus*", Phytochemistry, 20(8)1883-1885 (1981).

Strome, et al., "Heterozygous screen in *Saccharomyces cerevisiae* identifies dosage-sensitive genes that affect chromosome stability." Genetics, 178(3): 1193-1207 (2008).

Su and Tamm, "Synthesis studies towards Pseurotin A", Helvet. Chim. Acta., 78:1278-1290 (1995).

Sussmuth, et al., "Effects of test conditions and interfering factors on sensitivity of bacterial tests based on inhibition of growth and motility," Environmental Toxicology and Water Quality, 7(3):257-74 (1992).

Tsai, et al., "Cytotoxic butanolides from the stem bark of Formosan *Lindera communis*", Planta Med. , 67(9):865-7 (2001).

Tschesche, et al, "Uber the antibiotisch wirksamen substanzen de tulpe tulipa gesneriana," Tetrahedron Letters, 6:701-6 (1968).

Vilella, et al., "Inhibitors of farnesylation of Ras from a microbial natural products screening program," J Ind Microbiol Biotechnol., 25(6):315-327 (2000).

Viturro, et al., "Antifungal diastereomeric furanones from *Mutisia friesiana*: structural determination and conformational analysis", Tetra. Asymm., 12 (2001).

Willuhn, "Arnica flowers: pharmacology, toxicology, and analysis of the sesquiterpene lactones—their main active substance," in Phytomedicines of Europe: Chemistry and Biological Activity (Lawson, et al, eds.) Washington DC American Chemical Society, pp. 118-132 (1997).

Zampella, et al., "Amphiasternins: a new family of cytotoxic metabolites from the marine sponge *Plakortis quasiamphiaster*", Tetrahedron, 57(1):257-263 (2001).

Zapf, et al., "lncrusoporin, a new antibiotic from Incrustoporia carneola", Acta. Chem. Scand., 49:233-34 (1995).

Simon, et al., "Differential toxicities of anticancer agents among DNA repair and checkpoint mutants of *Saccharomyces cerevisiae*", Cencer Res, 60:328-33 (2000).

* cited by examiner

LACTONE FORMULATIONS AND METHOD OF USE

CROSS REFERENCE TO RELATED APPLICATIONS

This application is a continuation of pending prior application U.S. Ser. No. 11/139,338 filed May 26, 2005, entitled "Lactone Formulations and Method of Use", by David Terrero, which is a continuation of U.S. Ser. No. 10/172,462 filed Jun. 12, 2002, and claims benefit of and priority to U.S. Provisional Patent Application No. 60/297,875 filed Jun. 13, 2001, all of which are herein incorporated in their entirety by reference.

FIELD OF THE INVENTION

The present inventions are generally in the fields of pharmaceutically active lactones, their pharmaceutical formulations, and method of use thereof, and methods for the synthetic preparation of chemically functionalized lactones useful therefor as anticancer and antiinfective agents.

BACKGROUND OF THE INVENTION

Despite the development of many different compounds which are useful in the treatment of infection, cancer, and other disorders, there remains a need for the development of new compounds which may be effective at lower dosages, more selective, having fewer side effects or capable of treating diseases or disorders where resistance to the known compounds has developed.

Chemotherapeutic agents are used for the treatment of infections, cancer, abnormal proliferation disorders (endometriosis, restenosis, psoriasis), and other disorders. Most chemotherapeutic agents have side effects due to lack of specificity. For example, cancer is one of the leading causes of death. One of the primary modes of treating cancer, chemotherapy, is used specifically to limit cell growth and replication. Most chemotherapy agents also affect neoplastic and rapid proliferating cells of normal tissues (e.g., bone marrow, hair follicles, etc.), which results in several negative side effects including hair loss, nausea, vomiting, and suppression of bone marrow function. Moreover, effectiveness of these agents frequently diminishes over time due to the development of resistance.

It is therefore an object of this invention to provide a novel class of compounds effective as anti-infective and/or anti-proliferative agents.

It is another object of this invention to provide an effective antineoplastic agent with specific cytotoxicity in order to minimize side effects.

It is a further object of the present invention to provide antiinfective agents which are specific and different from many other drugs currently in use, to provide an alternative method of treatment for drug resistant organisms.

SUMMARY OF THE INVENTION

Compounds of Formulae Ia and Ic having a lactone structure and a methylene group at the alpha-position of the lactone structure have been discovered. The lactone compounds can be reacted with a neucleaphilic agent to open the lactone ring to a compound of Formula Ib. The lactone of Formula Ia and its functional derivatives have been isolated from *Securidaca virgata*. These compounds are referred to as LMSV-6 or Securolide™. The purified compounds have demonstrated activity in assays for anti-bacterial and anti-fungal activities, and for treating proliferation disorders such as cancer. Based on the in vitro assays, the lactones are useful for treating proliferation disorders including, for example, breast cancer, colon cancer, rectal cancer, stomach cancer, pancreatic cancer, lung cancer, liver cancer, ovarian cancer, esophageal cancer, and leukemia. They are also effective for treatment of bacterial and fungal infections, including treatment of peptic ulcer disease, gingivitis and periodontitis.

The method for making a compound of Formulae Ia and Ic generally involves: a) providing a precursor having a lactone structure, and b) reacting the precursor with one or more chemical reagents to provide a product having a methylene group at the α-position of the lactone structure. The product can be treated with a neucleaphilic agent such as an alcohol, alkoxide, amine, or any other neutral or anionic neucleaphiles to generate a compound of Formula Ib.

DETAILED DESCRIPTION OF THE INVENTION

I. Lactone Compositions

A. Lactones Isolated from *Securidaca virgata*.

Lactones with an exocyclic methylene group and their respective derivatives with a hydroxyl in gamma position are disclosed. The lactones and the derivatives thereof can be synthesized or isolated from natural resources. In one embodiment, the lactones and the derivatives can be isolated by means of chromatographic methods, from a plant whose taxonomic scientific name is *Securidaca virgata*, which belongs to Polygalaceae as its botanical family. As used herein, the term "lactones" encompasses any organic chemicals having a five-member ring lactone structure in which the oxygen atom of the C=O group can be replaced by a sulfur atom or a nitrogen grouping. The term "derivatives" as used herein refers to any compounds that are made from the lactones by reacting the lactones with one or more chemical reagents. The term also refers to any products obtainable by ring opening of the lactones with an organic or inorganic neucleaphilic agents to form, for example, an acid, ester, amide, or any other products thereof.

In one embodiment, the lactone has the following chemical structure:

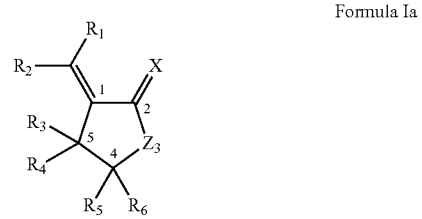

Formula Ia wherein $R_1$-$R_6$ taken independently or $R_3$-$R_6$ taken together are a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteroatom such as oxygen, sulfur, or nitrogen grouping in linear, branched, or cyclic structural formats; and X is a heteroatom such as oxygen, sulfur, or nitrogen grouping in linear, branched, or cyclic structural formats.

In another embodiment, the compound has the following chemical structure:

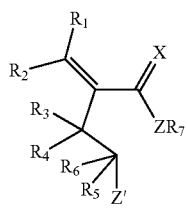

Formula Ib wherein $R_1$-$R_7$ taken independently or $R_3$-$R_6$ taken together may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

X is a heteroatom such as oxygen, sulfur, or nitrogen grouping in linear, branched, or cyclic structural formats;

Z is a heteroatom such as oxygen, sulfur, or nitrogen grouping in linear, branched, or cyclic structural formats; and Z' may a hydrogen atom, a halogen atom, a hydroxyl group, or any other organic composition containing from 1-8 carbon atoms and optionally include a heteroatom such as oxygen, sulfur, or nitrogen grouping in linear, branched, or cyclic structural formats.

In still another embodiment, the lactones having an alpha-methylene group can have the structure as show below:

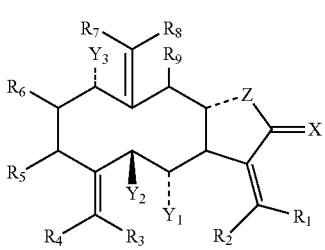

Formula Ic wherein $R_1$-$R_9$ taken independently or $R_5$ and $R_6$ taken together may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

$Y_1$, $Y_2$, and $Y_3$ taken independently or $Y_1$ and $Y_2$ taken together may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteroatom such as oxygen, sulfur, or nitrogen grouping in linear, branched, or cyclic structural formats; and X is a heteroatom such as oxygen, sulfur, or nitrogen grouping in linear, branched, or cyclic structural formats.

In one embodiment, the lactone is a securolide, which is a alpha-methylene-lactone (1) having the structure:

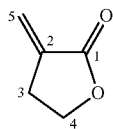

In another embodiment, the ester is methyl α-methylene-γ-hydroxy-butanoate (2) as shown in the following structure:

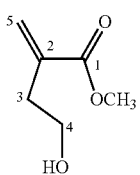

In still another embodiment, the lactone is a bicyclic compound having the following structure:

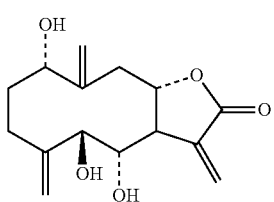

(4')

B. Excipients

The lactone and functional derivatives can be formulated using standard techniques for enteral, parenteral, or topical administration. Effective dosages can be determined based on the in vitro assays known to those skilled in the art, such as the assays described in the examples.

Suitable pharmaceutically acceptable vehicles for parenteral delivery include sterile saline, phosphate buffered saline, and standard microparticulate formulations for injection, including polymeric microspheres, microcapsules, liposomes, and emulsions. These can include degradable polymers such as polylactic acid and polyglycolic acid, and copolymers thereof, polyanhydrides, polyorthoesters, polyhydroxyalkanoates. For injection, the lactones will typically be formulated as solutions or suspensions in a liquid carrier.

For topical delivery, the lactone may be formulated in an ointment, lotion, gel, spray, or controlled or sustained release formulation (such as a transdermal patch).

For enteral delivery, the lactone may be formulated in a tablet, capsule, suspension or solution, dissolved or encapsulated in an excipient such as a sugar like lactose, inert compound such as magnesium stearate, paraffin derivatives, glycols or gum arabic. The formulations may further include dyes, flavorings, preservatives, dispersing or emulsifying agents, or materials modifying release or stability properties of the formulations.

The active compound may be used in combination with a second pharmaceutically acceptable antimicrobial agent, such as nitroimidazole antibiotics, e. g. tinidazole and metronidazole; tetracyclines, e. g. tetracycline, doxycycline and minocycline; penicillins, e. g. amoxicillin and meziocillin, cephalosporins, e. g. cefaclor, cefadroxil, cephadrine, cefuroxime, cefuroxime axetil, cephalexin, cefpodoxime proxetil, ceftazidime and cefatriaxone; carbapenems, e. g. imipenem and meropenem; aminoglycosides, e. g. paromomycin, macrolide antibiotics, e. g. erythromycin, clarithromycin and azithromycin; lincosamide antibiotics, e. g. clindamycin; rifanycins g. rifampicin, and nitrofurantoin.

Combinations of the compounds with a pharmaceutical acid-lowering agent may used in the treatment of acid-related disorders, such as acid pump inhibitors, e. g., omeprazole and lansoprazole, or $H_2$ antagonists, e. g., ranitidine, cimetidine, and famotidine.

II. Synthesis of Lactones

The synthesis of the lactones and their respective derivatives involves the step of forming an alpha-methylene group. Generally, the method for making a compound of Formulae Ia and Ic involves: a) providing a precursor having a lactone structure, and b) reacting the precursor with one or more chemical reagents to provide a product having a methylene group at the α-position of the lactone structure. The product can be treated with a neucleaphilic agent such as an alcohol, alkoxide, amine, or any other neutral or anionic neucleaphiles to generate a compound of Formula Ib.

Methods of forming the methylene group are standard techniques well documented in synthetic organic chemistry (see, for example, March, "Advanced Organic Chemistry," 4th Edition, 1992, Wiley-Interscience Publication, New York). The lactones can be synthesized, for example, by starting from a five-member lactone and then derivatizing the alpha position to add a methylene group onto the molecule.

For example, as shown by Scheme 1, reacting a compound having the structure (1) with a base, an alcohol and a ester produces an enolate, which is a precursor to lactone of structure (4) (See Scheme 1).

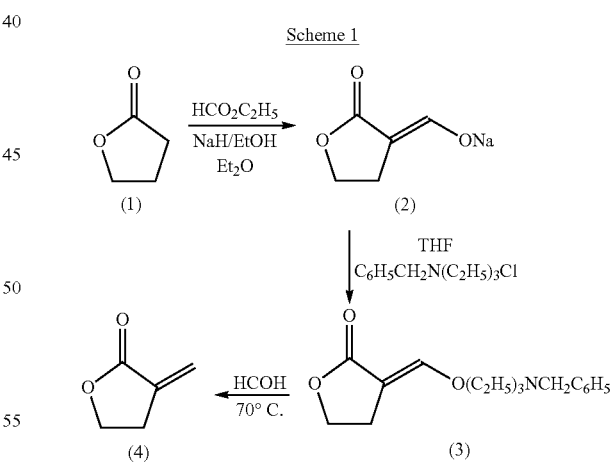

Scheme 1

The lactone (4) can be further derivatized using standard synthetic techniques available in the art of organic synthesis (see, for example, March, Supra). For example, carboxyl group functionalized lactones (4) can be prepared by, for example, reacting a compound having the structure (1) with an agent for alpha carboxylation of lactones (MMC, methyl-Mg-carbonate), and an aldehyde in the presence of a base such as triethylamine to yield the lactone of structure (4), which is the isolated naturally occurring lactone (Scheme 2).

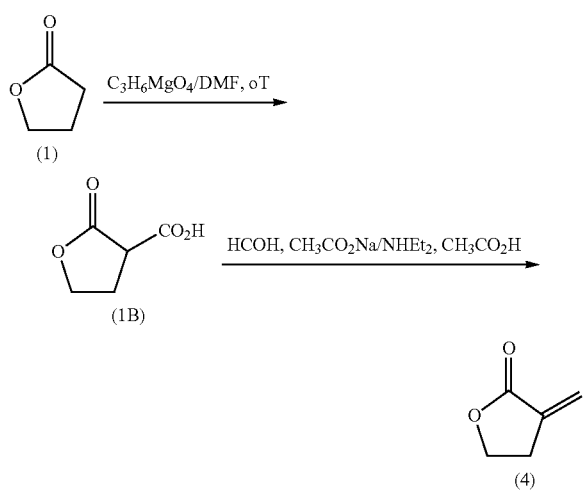

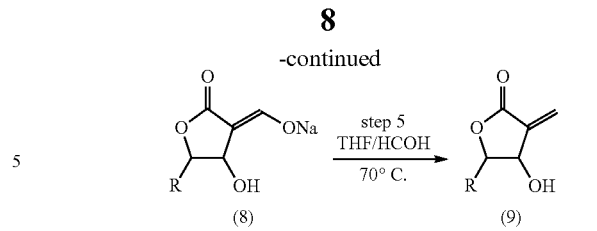

More functionalized lactones can be prepared by readily available synthetic method in the art (see, for example, March, "Advanced Organic Chemistry," 4th Edition, 1992, Wiley-Interscience Publication, New York). For example, functionalized lactones (4) can be prepared by reacting a compound having the structure (1) with a base, an alcohol and a ester to produce an enolate, which is a precursor to lactone of structure (4) (Scheme 4).

In Scheme 2, a functionalized methylene group lactone (4), is prepared by reacting a compound having the structure (1) with methyl-Mg-carbonate (MMC), an aldehyde in a buffer with a base NN-Dimethylformamide [DMF-HCON(CH$_3$)$_2$], to produce a carboxylic acid functionalyzed lactone (1B), and lactone (1B) is then treated with an aldehyde and Diethylamine, Sodium Acetate, Acetic Acid to produce lactone (4).

Other functionalized lactone derivatives can be readily prepared. For example, a functionalized derivative lactone (9) can be prepared by reacting a compound having the structure (5) with an inorganic acid and an alcohol by heating to reflux to produce an enol-lactone, which is then reduced with a base to produce a product of structure (7). Reaction of (7) with a base, an alcohol and a ester produces an enolate, which is a precursor to functionalized lactones of compound (9) (Scheme 3).

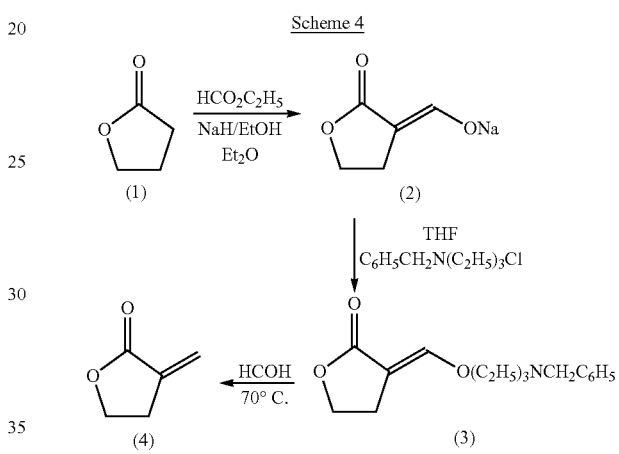

Scheme 4

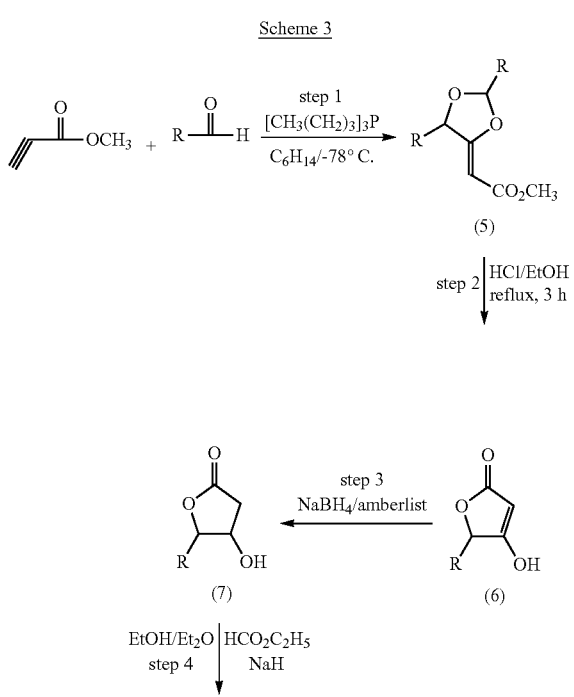

The pharmaceutically acceptable salts of the lactone compounds of the Formulae Ia-c, if in the form of an acid or a base such as an amine, can be prepared in a conventional manner by treating a solution or suspension of the compound of Formulae Ia-c with about one chemical equivalent of a pharmaceutically acceptable base or acid. Conventional concentration and recrystallization techniques are employed in isolating the salt.

III. Methods of Treatment

A. Disorders to be Treated

Based on the activities determined as described in the examples, the lactones are useful as anti-infectives and anti-proliferatives. In particular, the lactones can be administered in an effective amount to inhibit bacterial or fungal growth, viral disease or to treat a bacterial or fungal disease. Examples of preferred bacterial disorders to be treated include peptic ulcer disease, gastritis, dyspepsia, periodontal disease and gingivitis. Fungicidal compositions are comprised of a fungicidally effective amount of a compound of formula 1 or a salt thereof and an inert pharmaceutical carrier. Examples of the pharmaceutical composition may be plain or sugar-coated tablets, gelatin capsules, granules, suppositories, injectable preparations, ointments, creams or gels.

The fungicidal compositions are useful particularly on *Saccharomyces cerevisiae, Candida albicans* and other *Candida* such as *Candida glabrata, krusei, tropicalis, pseudotropicalis* and *parapsilosis*, on *Aspergillus fumigatus, Aspergillus flavus, Aspergillus niger, Cryptococcus neoformans, Microsporum canis, Trichophyton rubrun, Trichophyton mentagrophyte* and to combat particularly digestive, urinary, vaginal or cutaneous candidosis, cryptococcosis, for example, neuromeningeal, pulmonary or cutaneous cryptococcosis, bronchopulmonary and pulmonary aspergillosis and invasive aspergillosis of the immunodepressive system. The compositions can also be used in the prevention of mycotic affections in congenital or acquired immunological suppressions.

The lactones can also be administered to treat proliferative disorders, including cancers. Representative types of cancers which have shown inhibition in cell growth or proliferation include breast cancer, lung cancer, ovarian cancer, esophageal cancer, and leukemia. Other types of abnormal proliferative disorders that the lactones may be useful in the treatment of include endometriosis and restenosis, caused by abnormal overproliferation of endothelial tissue following angioplasty.

The functionalized lactone (9) above is particularly useful as an aspartic protease inhibitor, and has been demonstrated to inhibit the aspartic protease of HIV-1, and thereby limit viral processing, and in particular post-translational processing of the viral gene products (gag/gag-pol).

These lactones are also useful in modulating pain response through its activity as a neurotransmitter.

B. Dosages

The effective amount will be determined based on the disease or disorder to be treated, the mode of administration and the formulation. Effective dosages can be routinely determined based on the effective dosages determined using in vitro assays such as those described in the examples.

The high activity of Securolide (LMSV-6) against *Escherichia coli, Klebsiela pneumoniae, Pseudomona aeroginosa, Staphylococcus aureus*, and its low molecular weight are advantageous. Advantages of Securolide include its facility and speediness to promote pharmacologic response; its possibility to cross over cellular membrane barriers, where high molecular weight is the main hindrance, and its potent activity against *Pseudomonas*, which is one of the more drug resistant microorganisms.

The method for combating fungal infections comprises administering a fungicidally effective amount of a compound of formula I or an acid addition salt thereof by buccal, rectal, parental route, or by local route as a topical application on the skin and mucous membranes, but the preferred route is the buccal route. The usual daily dose is 1 to 5 mg/kg depending on the method of administration, the condition treated and the specific compound.

The compounds may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking liquid in a concentration of about 5 to 5000 ppm, preferably about 25 to about 500 ppm They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1 to about 50 mg/kg/day, preferably about 0.2 to about 10 mg/kg/day given in a single daily dose or up to 4 divided doses.

The compounds can be administered to humans for the treatment of *H. pylori* infections by either the oral or parenteral routes and may be administered orally at dosage levels of about 0.1 to about 50 mg/kg, advantageously about 0.5 to 50 mg/kg/day given in a single dose or up to 4 divided doses. For intramuscularly or intravenously administration, dose levels are about 0.1 to about 100 mg/kg/day, preferably about 0.5 to about 50 mg/kg/day. While intramuscularly administration may be a single dose or up to 4 divided doses, intravenous administration can include a continuous drip. Variations will necessarily occur depending on the weight and condition of the subject being treated and the particular route of administration chosen as will be known to those skilled in the art.

The second antimicrobial agent and the acid-lowering agent may be administered with the compounds in the same manner as discussed above for the compounds of the invention. Thus, depending on the particular agent, administration may be orally at about 0.1 to about 500 mg/kg, for instance at about 1 to 3 grams per day of second antimicrobial agent, and about 40 to 80 mg per day of the acid-lowering agent, or by injection at about 0.1 to about 200 mg/kg/day.

The present invention will be further understood by reference to following non-limiting examples.

Example 1

Isolation of Lactone from *Securidaca virgata*

*Securidaca virgata* roots were collected at San Cristobal Dominican Republic. A sample voucher of aerial part was sent to National Botanic Garden in order to be identified. Air dried, chopped and milled roots (253 g) were extracted in a Soxhlet apparatus. The cold extract was filtered and then concentrated in vacuo (55° C.) to afford a syrupy liquid (29.76 g) that means 11.76% of yield. This syrup (28 g, tested microbiologically) was treated with 300 ml of Sulfuric acid 0.5M and stirred for 4 hours and then extracted in a liquid-liquid extraction with chloroform successively until the syrup was separated from the acid chloroform soluble matter. Then the hydrosoluble phase was basified with Ammonium hydroxide 20% (pH=8-9) and the hydrosoluble phase extracted again with chloroform. The chloroform extract was concentrated in vacuo (50° C.), to yield an extract of 5.92 g (yield=21.14% with regard to crude extract and 2.33% with regard to roots extracted). The 5.92 g had a purity of 95.34% LMSV-6 (Securolide™). The final chloroform extract (5.92 g) were chromatographed in basic alumna (63-150 μm) and eluted with petroleum ether-ethylacetate mixture (30:70). Fractions collected were concentrated to have a pure clear liquid substance (Securolide™) (1). Chromatographic fractions 72-97 (674 mg) from the liquid chromatographic column where (1) was isolated was again chromatographed to obtain an amber colored liquid (2). Compound (1) and (2) were then tested in bioassays.

Spectroscopic analysis yielded the following data for compound (1):

Physical Data
RELATIVE DENSITY: 1.070 g/mL pH=5.853
REFRACTIVE INDEX=1.471
Spectral Data
Mass spectrometry: MS m/z (rel. Int,): molecular ion 98.0 [M$^+$], (54), 68 (100), molecular formula $C_5H_6O_2$.
Infrared Spectroscopy (IR): 1761.6 cm$^{-1}$ (lactone), 1667 cm$^{-1}$ (C=C) 810 cm$^{-1}$" (C=CH$_2$).

Proton Nuclear Magnetic Resonance (NMR¹H, 200 MHz, CDCI₃: δ 2.98 ppm (2H multiplet), 4.37 ppm (1H triplet, J=7.4 Hz), 5.65 (1H triplet, J=2.6 Hz), 6.22 (1H triplet, J=2.6,)
Carbon 13 Nuclear Magnetic Resonance (NMR¹³ C 200 MHz, CDCI₃): δ 170.7 (C-1), 133.3 (C-2), 27.4 (C-3), 65.5 (C-4), 122.2 (C-5)
Double Nuclear Magnetic Resonance Protonic Experiments (Irradiations) double Nuclear Magnetic Resonance Proton Experiments showed coupling between each one of existing protons. Methylenic exocyclic protons δ (5.65 and 6.22), irradiation of C-3 showed coupling with C-4 and in this way were determined all protons connectivity of (1).

Spectroscopic analysis yielded the following data for compound (2):
Mass Spectrometry: 130.0 (M+, 3), 113 (M+-OH, 12), $C_6H_{10}O_3$.
Infrared Resonance (IR): 3614.6 cm⁻¹ (OH), 1629 cm⁻¹ (C=C) 1150.9 (—CO—OCH₃), 810 cm⁻¹ (C=CH₂).
Proton Magnetic Nuclear Resonance Spectrometry (200 MHz, CDCI₃): δ 2.54 ppm (2H td J=6.26 Hz), 3.73 (s), 3.72 (2H, t J=6.26 Hz), 5.65 (1H t, J=1.2 Hz), 6.21 (1H t, J=1.2 Hz).
Carbon¹³ Magnetic Nuclear Resonance Spectrometry (200 MHz, CDCI₃): δ 167.8 (C-1), 137.2 (C-2), 35.4 (C-3), 61.3 (C-4), 127.3 (C-5), 51.93 (C-6).
Ampoules consisting of a pharmaceutical composition containing the compound of the formula 1 (Securolide) had the following ingredients:
Original Quantity: 750 Amp

| Raw material | Weight | UM |
|---|---|---|
| LMSV-6 (Securolide) | 51.7900 mL | 6.27% |
| Sesame oil | 760.8200 mL | 92.20% |
| Bencilic Alcohol U.S.P. | 12.3750 mL | 1.50% |
| Total Volume | 824.9850 mL | 99.97% |

| | |
|---|---|
| Peptone | 1.0 g |
| Digestive pancreatic Caseine | 4.0 g |
| Yeast Extract | 3.0 g |
| Beef Extract | 1.5 g |
| Dextrose | 1.0 g |
| Agar | 15.0 g |
| pH after sterilization | 66 ± .01 |

Culture Medium for *Pseudomonas aeroginosa* (USP 23 <81>)

| | |
|---|---|
| Pancreatic digestive Casein | 17.0 g |
| soy Papain digestive | 3.0 g |
| Sodium Chloride | 5.0 g |
| Dibasic Potassium Phosphate | 2.5 g |
| Dextrose | 2.5 g |
| Agar | 20.0 g |
| Water to make about | 1.0 Lit |
| pH after sterilized | 7.2 ± 0.1 |

Culture Medium for *Escherichia coli* and *Klebsiella pneumoniae* (USP 23 <81>)

| | |
|---|---|
| Peptone | 5.0 g |
| Yeast Extract | 1.5 g |
| Beef Extract | 1.5 g |
| Sodium Chloride | 3.5 g |
| Dextrose | 1.0 g |
| Dibasic Potassium Phosphate | 3.68 g |
| Monobasic Potassium Phosphate | 1.32 g |
| Water To make about | 1.0 Lit |
| pH after sterilized | 7.0 ± 0.05 |

| | LMSV- | Concentration (μL/10 mL) | | | | | | | |
|---|---|---|---|---|---|---|---|---|---|
| Bacteria | 6 (puro) | 0 | 20 | 30 | 40 | Ciprof | Fosf | Dis(−) | Dis(+) |
| *E. coli* | 30 (mm) | — | — | — | — | 28 | 10 | — | — |
| Kleb | 40 | — | — | — | — | 26 | 22 | — | — |
| Ps. A | 30 | — | — | — | — | 12 | 6 | — | — |
| St. a | 30 | — | — | — | — | 20 | 18 | — | — |
| Str. P | — | N/A | N/A | N/A | N/A | N/A | N/A | N/A | N/A |

Example 2

Assays for Anti-Bacterial Activity

The material obtained in Example 1 was screened for antibiotic activity against *Staphylococcus aureus, Pseudomonas aeroginosa, Escherichia coli*, and *Klebsiella pneumoniae*.
Materials and Methods:
Solvent: Buffer Phosphate 0.1 N, pH=8.0
Antibiotic: LMSV-6 (Pure, Securolide)
Medium coat: 2 mL/100 mL
Inoculum: 4 mL/Petri Dish
Preparation of Culture Medium:
Culture Medium for *Staphylococcus aureus* (USP 23 <81>)

Unit to measure zone of inhibition is millimeters (mm)
Ciprof=Disc of sensitivity Ciprofloxacina 5 micrograms
Fosf=Disc of sensitivity Fosfomicina 50 micrograms
Dis(−)=Disc of sensitivity with no substance applied
Dis(+)=Disc of sensitivity with 20 microliters of Tween 60 at 2%
N/A=not done Test
Microorganisms used were standardized by American Type Culture Collection (ATCC), used in first generation:
*E. coli* ATCC 352 18, Lot 202602, Exp. May 2000 (19-258)
*Kleb. Klebsiela pneumoniae*, ATCC 13882, Lot 202 174, Exp February 2000 (19-152)
*Ps. A Pseudomona aeroginosa* ATCC 27853, Lot 202992, Exp August 2000 (19-060)

*St. A *Staphylococcus aureus* ATCC 12598, Lot 202564, Exp May 2000 (19-137)
**Str. P *Streptococcus pyogenes*, ATCC 21547, Lote 202691, Exp June 2000 (19-190)
*=Atmospheric oxygen, Temp=35+2° C.
**=Atmospheric $CO_2$, Temp=35±2° C.

Results:

5 microliters of LMSV-6 (Securolide) inhibits growth of *Escherichia coli, Klebsiela pneumonae, Pseudomonas aeroginosa* and *Staphylococcus aureus*.

Dilutions:

10 microliters/10 mL, (0.001 microliters/ml)
20 microliters/10 mL, (0.002 microliters/mL)
30 microliters/10 mL (0.003 microliters/mL)
and 40 microliters mL (0.004 microliters/mL)
of LMSV-6 in 10 mL Tween 60-2% did not exhibit inhibition of bacterial growth, indicating that these concentrations are below the Minimum Inhibitory concentration (MCI).

Example 3

Determination of Minimum Bacterial (*Sarcina lutea* and Inhibitory Concentration, MIC, LMSV-6 (Securolide)

Materials and Methods:

Methodology: Poured in plate, medium Mueler Hinton pH=8
Buffer pH=8 for ceftriaxone pattern dilution
Tween 20 at 2% for LMSV-6 (Securolide) dilution
Microorganism: *Sarcina lutea*
Sample(s): LMSV-6 (16.0 microliters/100 mL and 10 microliter applied to sensitivity disc).
Methodology: Poured in plate, medium Mueler Hinton p&8
Buffer pH=8 for ceftriaxone pattern dilution
Tween 20 at 2% for LMSV-6 (Securolide) dilution
Used Microorganism: *Sarcina lutea*
Sample(S): LMSV-6 (10 microliters/mL and 20 microliter applied to sensitivity disc)
Control Pattern (P): Ceftriaxone (disc with 10 mcg)
Results:

| APPLIED VOLUME TO DISC | ZONE OF INHIBITION |
|---|---|
| 5 microliters | 42.0 mm |
| 1.6 microliters | 20.0 mm |

There was no significant zone of inhibition, therefore the Minimum Inhibitory Concentration is close to 0.2 microliters of LMSV-6. The approximate MIC is 0.2 microliters of LMSV-6 3.3 mm inhibition Example 4

In Vivo Treatment of Bacterial Infection

Rats were infected in surgery and then successfully treated with Securolide using doses calculated based on comparison with ceftriaxone.

Example 5

Assays for Anti-Neoplastic Activity

Materials and Methods:

There are a large number of biological assays that require the measurement of surviving or proliferating mammalian cells. This can be achieved by different methods, e. g. counting cells that exclude or include a dye; measuring released $^{51}Cr$ labeled protein after cell lysis; and measuring incorporation of radioactive nucleotides radioactive [$^3H$]thymidine) or [$^{125}I$]iododeoxyuridine) during cells proliferation.

Viable cells can be measured by using any of several staining methods, but a more accurate method is the multiwell scanning spectrophotometers (ELISA readers) which can measure large number of samples with a high degree of precision.

A colorimetric assay to detect living cells, utilizing a colorless substrate that is modified to a colored product by any living cell, but not by dead cells or tissue culture medium, was used. The assay uses Tetrazolium salts MIT [3-(4,5-dimethylthiazol-2-yl)-2,5 diphenyl tetrazolium bromide] to measure the activity of various dehydrogenase enzymes (Slater et al. 1963). The Tetrazolium ring is cleaved by active mitochondria, so this reaction only occurs in living cells. The cleavage of MTT into Formazan by the mitochondrial enzyme succinate dehydrogenase produces a dark blue colored compound (Formazan) whose amount is proportional to the number of cells present. The Formazan concentration in a gradient of Securolide concentrations was measured by multiwells scanning spectrophotometer (ELISA reader). Data analysis was then used to establish the Inhibitory concentration fifty ($IC_{50}$) which is a quantitative parameter of antineoplastic activity. Different cancer cells lines were tested in order to measure indirectly the cytotoxic or antineoplastic activity (surviving cells) of LMSV-6 (Securolide). Cancer cell lines that were tested included HEP 2 (Laringe carcinoma) and HELA (Cervix Carcinoma).

Materials:

Culture Medium (DMEN+all)
EDTA
Trypsin-EDTA
DMEM+ALL and 10% TERNERO RECENTAL SERUM.
Dimethyl sulfoxide
MTT [3-(4,5-dimethylthiazol-2-yl)-2,5-diphenyl tetrazolium bromide]
Multiwell scanning spectrophotometers (ELISA readers)

Methods:

Cells were cultured using standard techniques. See, for example, R. Ian Freshney "Culture of Animal Cells" A Manual of Basic Technique (Alan R Liss, Inc., New York, Second Edition) p. 245-256.

Assessment of cell growth inhibition was determined according to the methods of Skehan et aL, J. Nat. Cancer Inst. 82, 1107 (1990). Cells were plated between 400 and 1200 cells/well in 96 well plates and incubated at 37° C. for 15-18 h prior to drug addition to allow attachment of cells. Compounds tested were solubilized in 100% DMSO and further diluted in RPMI-1640 containing 10 mM HEPES. Each cell line was treated with 10 concentrations of compounds (5 log range). After a 72 H incubation, 100 ml of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 mL) was added to each well. Following a 5 min incubation at room temperature, plates were rinsed 5 times with 0.1% acetic acid and air dried.

Bound dye was solubilized with 10 mM Tris Base (pH 10.5) for 5 min on a gyratory shaker. Optical density was measured at 570 nm.

See also Gerlier, et al. J. Immunol. Meth. 94, 57-63 (1986); Slater, et al., Biochim. Biophys. Acta, 77, 383-393 (1963); Kasugai, et al., Japan J: Pharmacol. 52, 95-100 (1990); Mosmann J. Immunol. Methods, 65, 55-63 (1983); Denizot, et al., J. Immunol. Methods, 89, 271-277 (1986).

Data were fit with the Sigmoid-Emax concentration-Effect model (see Holford, N. H. G.: Scheiner, L. B., "Understanding the dose-effect relationship: Clinical applications of pharmaco-kinetic-pharmacodynamic models.", Clin. Pharimiacokin. 1981, 6,429-453) with non-linear regression, weighted by the reciprocal of the square of the predicted response. The fitting software was developed by the Roswell Park Institute with Microsoft FORTRAN, and uses the Marquardt algorithm (see Marquardt, D. W., "An algorithm for least squares estimation of nonlinear parameters", J. Soc. Ind. Appl. Math. 1963, 11, 431-441) as adopted by Nash (see Nash J. C., "Compact numerical method for computers: Linear algebra and function minimization". John Wiley & Sons, New York, 1979) for the non-linear regression. The concentration of drug which resulted in 50% growth inhibition ($IC_{50}$) was calculated.

Results:
LMSV-6 CYTOTOXIC ASSAY IN HEP-2 CELLS POPULATION OF $10^5$ Cells/mL (LARINGE CARCINOMA)
r=0.9878
$IC_{50}$=10.38μ/mL
LMSV-6 CYTOTOXIC ASSAY IN HEP-2 CELLS POPULATION OF $10^6$ Cells/mL (LARINGE CARCINOMA)
r=0.9941
$IC_{50}$=37.37 μg/mL
LMSV-6 CYTOTOXIC ASSAY IN HELA CELLS POPULATION OF $10^5$ Cells/mL (CERVIX CARCINOMA)
r=0.9950
$IC_{50}$=7.37 μg/mL
LMSV-6 CYTOTOXIC ASSAY IN HELA CELLS POPULATION OF $10^6$ Cells/mL (CERVIX CARCINOMA)
r=0.9941
$IC_{50}$=27.30 μg/mL Example 6

Testing for Inhibition of *H. pyelori*

Materials and Methods:

Agar Dilution of Antimicrobial compound: 6 mg. of the compound to be evaluated is solubilized in 0.6 ml 100% dimethylsulfoxide (DMSO) and then brought up to 6 ml with sterile brucella broth. The final concentration of DMSO is 10% of the total volume. Serial 2-fold dilutions (3 ml Securolide+3 ml brucella broth) are then made in sterile brucella broth. A 2 ml aliquot of each broth dilution within the series is placed in separate sterile petri dishes, to which 18 ml of melted and cooled (approx. 50° C.) brucella agar supplemented with 7% horse blood is added. This yields a final 1:10 dilution of Securolide in agar, and a final concentration of DMSO of 1%. For example, if the highest concentration of drug in agar is 100 μg/ml. Agar plates can be prepared one day prior to inoculating, and refrigerated overnight.

Inocula Preparation: *Helicobacter pylori* cultures were maintained on trypticase soy-5% sheep blood agar plates, and transferred every 48 hours. *Helicobacter mustelae* cultures were maintained on the same agar and transferred every 48-60 hours, depending upon the extent of the growth of the previous transfer. Plates are incubated at 37° C. in GasPak jars with water-activated (10 ml) CampyPak Plus (BBL Microbio. Systems) envelopes with palladium catalyst.

*Helicobacter* cultures can be grown in brucella broth supplemented with 10% fetal calf serum in 10 ml volumes in deep petri dishes. The plates are incubated for 18-20 hours at 37° C. in GasPak jars with water-activated (10 ml) CampyPak Plus envelopes with palladium catalyst on a shaker at 50 rpm.

Overnight cultures (approximately $10^8$ CFU/ml) are diluted 10-fold in brucella broth (no FCS) in screwcapped tubes for use as the standard inoculum. The wells of a Steer replicator are filled with 0.8 ml of the diluted organism, and approximately $2 \times 10^4$ cells in 0.002 ml are placed on the agar surface. Inoculated plates are placed in a GasPak jar to which water-activated (10 ml) Campy Pak Plus envelopes with palladium catalyst have been added, and incubated at 37° C. for 48 hours.

Results:

Following incubation, all test plates are compared to a Securolide-free growth control plate. The MIC is the concentration which inhibits growth compared to the control plate. A thin film of growth might be visible at higher concentrations but this is discounted, and not considered the true MIC. Control organisms are also inoculated on each plate, and these are diluted 1000-fold for use as inocula. The control organisms include *Campylobacter jejuni*, and the screening cultures of *E. coli* [ATCC 35218, Lot 202602, Exp May 2000 (19-258)], *Pseudomona aeroginosa* [ATCC 27853, Lot 202992, Exp August 2000 (19-060)], *E. cloacae, Providencia stuartii* and *P. rettgeri*. Plates and/or inocula transfers should not be out of the microaerophilic environment longer than 2 hours. All manipulations involving *Helicobacter* cultures was performed in a laminar flow hood to decrease the chance of contaminating the cultures with mold.

The mouse model of Lee et al., Gastroenterology, 99, 1315-23 (1990) is used to predict the in vivo activity of a compound against *H. pylori* in humans.

*Helicobacter felis* is grown in brucella broth with 10% fetal bovine serum. A frozen culture is quickly thawed; the culture is checked for motility and 0.5 mL of the thawed frozen culture is inoculated into a deep tissue culture dish containing 9.5 mL of the brucella/serum mix. The dishes are put into a Capy Pak jar [BBL] to insure a microaerophilic atmosphere. The jar is put on a rotary shaker at 60 RPM in a 37° C. incubator. After 18 hours there should be visible turbidity. The culture is checked for purity and motility under a (phase) microscope and then pooled into a flask. Swiss-Webster female mice (18-20 g) are fasted for 18 hours before infection. The mice are infected three times on alternate days during a single week. Dosing begins two weeks after the last dose of organism. Treatments are given once per day for fourteen consecutive days. Sacrifice is about three weeks after completion of therapy. For each mouse, the stomach is excised and opened along the greater curvature. A plug (a 3 mm Tissue section) is taken from the antrum region of the stomach. The plug surfaced is washed, minced, and dropped into a tube with 100 microliters of urease reagent. The urease reagent (pH 6.3-6.5) contains urea and phenol red. If *Helicobacter* is present, urease will break down urea producing a change of pH. Purple (alkaline) is positive for *Helicobacter*; red/yellow (no change) is negative. Any color change is recorded after 18 hours. There are usually twenty mice per treatment group; the percent positive for each group is recorded.

There are several methods used clinically to determine whether *Helicobacter pylori* is present in a human subject. These are employed for initial diagnosis of infection prior to treatment, as well as for determining the success of treatment in eradicating the organism from the patient.

The urea breath test involves ingestion of radiolabelled urea. *H. pylori* produces an urease enzyme which degrades urea; mammalian gastric cells do not contain this enzyme. Exhalation of labeled carbon dioxide (analyzed by mass spectrometry or radioactivity, depending on the isotope employed) therefore indicates that *H. pylori* is present.

Serology can also be used to assess infection with *H. pylori*. Detection of serum antibodies to *H. pylori*, such as IgG and IgA, is carried out using enzyme-linked immunosorbent assay (ELISA). Numerous different *H. pylori* proteins can be employed as antigens.

Endoscopy of the patient provides samples of tissue which can be cultured in a microaerophilic environment to diagnose *H. pylori* infection. Alternatively, the sample can be examined histologically by employing one of a number of stains such as Giemsa or hematoxylin-eosin. An urea test which takes advantage of the production of urease by *H. pylori*, can also be applied. This test relies on the formation of ammonia from the urea hydrolysis, which results in an observable change in pH, that is an indication of the eradication of *H. pylori*.
Results:

Comparison of patient condition by endoscopy before and after treatment with the compound of example 1 has shown a decrease or absence of *H. pylori*.

Example 7

Determination of Fungal Activity

Materials and Methods:
Methods

Anti-fungal Activity of the Product may be determined as follow. Female mice weighing 18 to 22 g were used and a quantity of *Candida Albicans* 44858 was administered into a vein in the tail at the rate of $10^6$ CFU per mouse (CFU: colony forming unit). The mice were separated into 5 batches of 5 mice and they were treated in the following manner:

One Hour after Infection group 1: the mice were treated with product at 25 mg/kg orally group 2: the mice were treated with product intraperitoneally at the dose of 25 mg/kg group 3: the mice were treated orally with Ketoconazole at 25 mg/kg group 4: the mice were treated intraperitoneally with Ketoconazole at a dose of 25 mg/kg group 5: the mice did not receive any anti-fungal treatment. The dead mice were counted over a period of 22 days.
Results:

The activity of product was excellent at the dose used in the two administration methods. The same treatments were also effective in the "topical model" with dermal fungi, for example trichophyton, and in the sublethal model.

Minimal Inhibitory Concentration (MIC)

*Candida albicans* cells were prepared as indicated in the J. Antimicrobial Chemotherapy 38, 579-587, and were washed 3 times with a 0.1 M phosphate solution and used immediately to determine the minimal inhibitory concentration (MIC). The MICs were determined by modification of a microtitre plate according to the standard method of the laboratory clinical standards of the Comite National.

RPMI-1640, and L-glutamine buffered at pH 7 with a 0.15 M solution of MOPS (3-[N-morpholino]propane sulfonic acid). *Candida albicans* cells ($1.5 \times 10^3$ cells/nil) were added to the wells of a 96-well plate containing RPMI-1640 and dilutions of antifungal agents. The results were read 48 hours after incubation at 35° C. and the MIC or the minimal inhibitory concentration which inhibited the growth of the *Candida albicans* cells was determined.

Minimal Fungicidal Concentration

After reading the MIC at 48 hours, the plates were shaken and 10 μl of well aliquot was removed from the wells which was placed on rectangular disks containing dextrose sugar. The plates were incubated for 48 hours at 35° C. and the minimal fungicidal concentration and the concentration of the antifungal agent at which there were no number of colony forming units.

Concomitant assays were made where LMSV-6 showed high activity against *Candida albicans*.

Example 8

Treatment of Periodontal Disease

It has been found that the Securolide is selectively effective against the specific anaerobic gram negative organisms associated with gingivitis, when topically applied to the affected gingiva.

The minimum inhibitory concentration (MIC) needed to kill *Bacteroides assaccharolyticus* (Forsyth strain), determined according to the procedure of Walker et al (Antimicrobial and Chemotherapy, Vol. 16, p. 452-457, (1979), is between 6 to 60 micrograms per ml. The MIC value for *B. gingivalis* is 6 micrograms per ml. The MIC value for *B. gracilis* and *Fusobacterium*, other gram negative organisms is about 25 for each; and the MIC value for the gram positive organism *Actinomyces viscosus* is 60 for the aerobic strain and 60 for the anaerobic strain.

I claim:

1. A method of treating an infection or a disease or disorder caused by an infection in a patient, the method comprising administering to a human patient in need thereof a pharmaceutical composition comprising a compound of Formula Ia

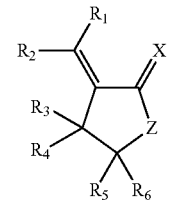

wherein $R_1$-$R_6$ taken independently are selected from the group consisting of hydrogen, $C_1$-$C_8$ alkyl, alkenyl, substituted alkenyl, alkynyl, substituted alkynyl, halogen, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, amino, substituted amino, sulfonyl, substituted sulfonyl, sulfonic acid, phosphoryl, substituted phosphoryl, phosphonyl, substituted phosphonyl, polyaryl, or substituted polyaryl;

Z is a heteroatom selected from the group consisting of oxygen, sulfur, and nitrogen; and X is a heteroatom selected from the group consisting of oxygen, sulfur, and nitrogen;

or a pharmaceutically acceptable salt thereof; and a pharmaceutical carrier for enteral, parenteral, or topical administration, wherein the pharmaceutical composition comprises an effective amount of the compound of Formula Ia to treat an infection or a disease or disorder caused by an infection.

2. The method of claim 1, wherein the infection is a bacterial infection.

3. The method of claim 1, wherein the infection is a fungal infection.

4. The method of claim 1, wherein the infection is a viral infection.

5. The method of claim 2, wherein the bacterial infection is caused by a bacteria selected from the group consisting of *Helicobacter pylori, Escherichia coli, Klebsiela pneumoniae, Pseudomona aeroginosa,* and *Staphylococus aureus.*

6. The method of claim 2, wherein the bacterial infection causes a disease or disorder selected from the group consisting of peptic ulcer disease, gastritis, dyspepsia, periodontal disease, and gingivitis.

7. The method of claim 3, wherein the fungal infection is caused by a fungus selected from the group consisting of *Saccharomyces cerevisiae, Candida albicans, Candida glabrata, Candida krusei, Candida tropicalis, Candida pseudotropicalis, Candida parapsilosis, Aspergillus fumigatus, Aspergillus flavus, Aspergillus niger, Cryptococcus neoformans, Microsporum canis, Trichophyton rubrun, Trichophyton mentagrophyte.*

8. The method of claim 3, wherein the fungal infection causes a disease or disorder selected from the group consisting of candidosis, cryptococcosis, and aspergillosis.

9. The method of claim 8, wherein candidosis is selected from the group consisting of digestive candidosis, urinary candidosis, vaginal candidosis, and cutaneous candidosis.

10. The method of claim 8, wherein the cryptococcosis is selected from the group consisting of neuromeningeal cryptococcosis, pulmonary cryptococcosis, and cutaneous cryptococcosis.

11. The method of claim 8, wherein the aspergillosis is selected from the group consisting of bronchopulmonary aspergillosis, pulmonary aspergillosis, and invasive aspergillosis of the immunodepressive system.

12. The method of claim 1, wherein the carrier for enteral administration is selected from the group consisting of a mouthwash, lozenge, tablet, capsule, solution, suspension, granule, and lollipop.

13. The method of claim 1, wherein the effective amount comprises a dose from about 0.1 to about 50 mg/kg/day.

14. The method of claim 13, wherein the dose is administered as a single daily dose or a divided daily dose.

15. The method of claim 1, wherein the carrier for topical administration is selected from the group consisting of a suppository, ointment, cream, gel, paste, colloidion, glycerogelatin, liniment, lotion, paste, plaster, powder, tape, patch, aerosol, solution, and tincture.

16. The method of claim 1, wherein the composition is suitable for administration by injection.

17. The method of claim 1, wherein the effective amount comprises a dose from about 0.1 to about 100 mg/kg/day.

18. The method of claim 17, wherein the dose is administered as a single daily dose or a divided daily dose.

19. The method of claim 1, wherein X is oxygen.

20. The method of claim 19, wherein the lactone is defined by the structure:

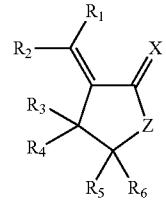

wherein $R_1$-$R_6$ are hydrogen atoms; Z is an oxygen; and X is an oxygen.

21. The method of claim 1, wherein the effective amount is from 1 to 5 mg/kg/day.

22. The method of claim 1, wherein the pharmaceutical composition further comprises one or more additional active agents.

* * * * *